US010500010B2

(12) United States Patent
Vayser et al.

(10) Patent No.: US 10,500,010 B2
(45) Date of Patent: Dec. 10, 2019

(54) MULTISPECTRAL LIGHT SOURCE

(71) Applicant: Invuity, Inc., San Francisco, CA (US)

(72) Inventors: Alex Vayser, Mission Viejo, CA (US); Gaston Tudury, San Francisco, CA (US); John Black, San Mateo, CA (US)

(73) Assignee: Invuity, Inc., San Francisco, CA (US)

( * ) Notice: Subject to any disclaimer, the term of this patent is extended or adjusted under 35 U.S.C. 154(b) by 578 days.

(21) Appl. No.: 15/159,723

(22) Filed: May 19, 2016

(65) Prior Publication Data
US 2016/0338795 A1 Nov. 24, 2016

Related U.S. Application Data

(60) Provisional application No. 62/163,592, filed on May 19, 2015.

(51) Int. Cl.
G02B 7/00 (2006.01)
A61B 90/30 (2016.01)
G02B 27/48 (2006.01)
G02B 26/00 (2006.01)

(52) U.S. Cl.
CPC .............. A61B 90/30 (2016.02); G02B 7/006 (2013.01); G02B 27/48 (2013.01); A61B 2090/309 (2016.02); G02B 26/008 (2013.01)

(58) Field of Classification Search
CPC ... A61B 90/30; A61B 2090/309; A61B 90/36; A61B 1/0684; A61B 5/0059
USPC ......................................................... 362/572
See application file for complete search history.

(56) References Cited

U.S. PATENT DOCUMENTS

| | | | |
|---|---|---|---|
| 2007/0138966 A1 | 6/2007 | Marka et al. | |
| 2008/0103390 A1* | 5/2008 | Contag | G01N 21/6428 600/427 |
| 2009/0227847 A1* | 9/2009 | Tepper | H05B 33/086 600/249 |
| 2009/0234234 A1 | 9/2009 | Machida | |
| 2012/0307081 A1* | 12/2012 | Dewald | G01J 3/10 362/231 |

(Continued)

FOREIGN PATENT DOCUMENTS

EP 2584251 4/2013

OTHER PUBLICATIONS

International search report with written opinion dated Aug. 31, 2016 for PCT/US16/33366.

*Primary Examiner* — William J Carter
(74) *Attorney, Agent, or Firm* — McDonnell Boehnen Hulbert & Berghoff LLP

(57) ABSTRACT

Medical illumination systems and devices for illuminating a target surgical area with a pre-selected type of multispectral light to aid tissue differentiation as viewed by the human eye, especially in open-surgery settings, and methods for practicing the same. A light source may have multiple settings selectable to provide various types of multispectral light configured to reduce reflection from corresponding tissue types relative to full-spectrum light. A pre-selected type of multispectral light may be configured to reduce reflection from blood. An illumination system or device can have one more illumination elements, including combinations of LEDs, lasers, and filtered broadband light sources. The multispectral light may be or comprise one or more of a continuous or pulsed wave.

34 Claims, 13 Drawing Sheets

(56) References Cited

U.S. PATENT DOCUMENTS

| | | | | |
|---|---|---|---|---|
| 2013/0010265 A1* | 1/2013 | Curtis | ............... | G02B 27/48 |
| | | | | 362/553 |
| 2013/0223056 A1* | 8/2013 | Hillendahl | ............ | F21V 21/005 |
| | | | | 362/223 |
| 2014/0316279 A1 | 10/2014 | Morishita | | |
| 2015/0069216 A1* | 3/2015 | Hutchin | ................ | G01J 1/4257 |
| | | | | 362/259 |
| 2015/0105769 A1 | 4/2015 | Makoto et al. | | |

\* cited by examiner

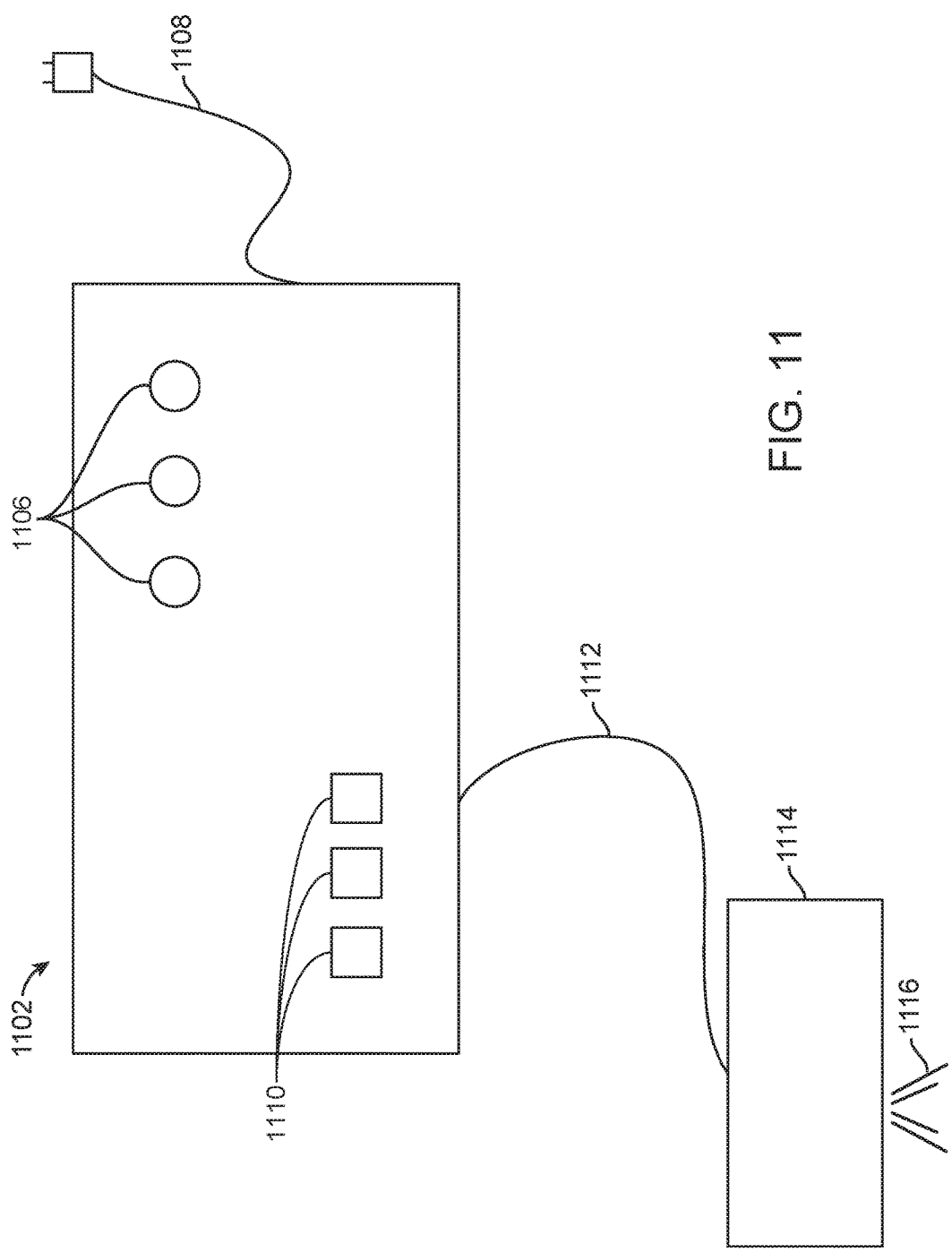

MULTISPECTRAL LIGHT SOURCE

CROSS-REFERENCE

This application claims the benefit of U.S. Provisional Application No. 62/163,592, filed May 19, 2015, entitled "MULTISPECTRAL LIGHT SOURCE", which application is incorporated herein by reference.

BACKGROUND

The field of the present invention generally relates to medical devices, systems and methods, and more particularly relates to light sources including, but not limited to, illumination sources used during surgical or other medical procedures.

Typically, surgical illumination is performed using white light sources. These sources of light are often based on xenon light engines that provide broad spectral response across most of the visible spectrum. In the last few years more LED (light emitting diode) light engines have become commercially available. The primary reason for this change has been for economic reasons. The cost of running an LED light engine is far less than a xenon light engine since bulbs do not need to be replaced.

A majority of the LED light engines currently on the market, such as Arthrex Synergy, utilize white light LED blue or UV phosphorous pumped dye. These light engines provide high color temperature and relatively high Color Rendering Index (CRI). CRI is a quantitative measure of a light source's ability to show the colors of a target accurately in comparison with an ideal or natural light source such as daylight. A high CRI is therefore typically desirable. There are also RGB (red, green, and blue) LED light sources such as the Stryker L9000, for example, that generate simulated white light by combining red, green, and blue LEDs. Since the light provided by this type of light source only has three spectral bands, which are separated by gaps between the bands, the CRI is often very low, and hence tissue illuminated with this light may not have the same color rendition when compared to xenon illumination. It would therefore be desirable to provide RGB LED or other light sources with higher CRI so that color rendition can be closer to natural colors.

In addition to color rendition, another challenge during surgery is that much of the tissue may become "bleached out" when high intensity pure white light sources are used. When the light is bright, many of the various tissue colors can become blended and color contrast dramatically reduced. It would therefore be desirable to create a light source that can enhance contrast by increasing absorption in certain tissues or reducing reflection in others, thereby improving tissue differentiation.

To improve contrast and tissue targeting, some manufacturers have used techniques to provide specific wavelengths of light to enhance visualization of specific tissue when a fluorescent injectable dye (e.g., indocyanine green (ICG)), is used. For example, filtered light, lasers and monochrome LEDs have been used in conjunction with injectable dye to illuminate tissue and cause it to fluoresce. However, this technique may complicate surgery when the light source is operating in a narrow wavelength and other tissues are not well seen. This may be the case when the entire image is monochrome in order to highlight the fluorescent tissue. Other systems try to address this challenge by adding imaging or computer imaging to combine the RGB image with the fluorescent image to provide a fused practical imaging environment.

For at least these reasons, it would be desirable to provide light sources which can provide a version of white light that may be used with endoscopic procedures, or in an open, direct visualization surgical procedure, without any image processing. It would also be desirable to provide a multispectral light engine that is based on multiple single color LEDs or other illumination elements working together to generate a specific spectral output. It would further be desirable to provide a light engine that allows the user to have certain pre-set settings that can easily be selected, based on surgical procedure, for example, in order to enhance the visibility of certain tissues and provide greater contrast without having to manually adjust the light source. At least some of these, and other objectives, may be addressed by various embodiments of the invention disclosed herein.

SUMMARY OF THE INVENTION

The present invention generally relates to medical systems, devices and methods, and more particularly relates to illumination sources that may be used to illuminate tissue during a surgical procedure.

According to an example embodiment of the present invention, a surgical illumination system for illuminating a target surgical area may be used to aid tissue differentiation. The surgical illumination system may be used with endoscopic applications, or in open-surgery settings where there is direct visualization of tissue, i.e., target tissue viewable by a human eye. The surgical illumination system may include a multispectral light source configured to provide light comprising a plurality of spectral bands. For example, the multispectral light source may provide light consisting of two or three bands. The multispectral light source may comprise at least one illumination element, for example, one or more of discrete color LEDs, lasers, filtered broadband light sources, or a combination thereof. For example, the at least one illumination element may be two or more distinct illumination elements, for example two discrete color LEDs. The at least one illumination element may comprise three LEDs, including a red LED, a blue LED, and a green LED.

The multispectral light source may have a plurality of spectral configuration settings. Each configuration setting may be selectable to provide a pre-selected type of light corresponding to the selection to be emitted from the multispectral light source. The pre-selected type of light may be configured to reduce reflection from a particular type of tissue of the target surgical area relative to a full-spectrum light of a similar intensity. For example, a pre-selected type of light may be configured to reduce reflection from blood or blood tissue.

In an example embodiment, at least one of the plurality of spectral configuration settings may correspond to a pre-selected type of light with substantially no visible light emission beyond 650 nm; with substantially no light emission between 650 nm and 730 nm; or with substantially no light emission at all beyond 650 nm.

In some example embodiments, the pre-selected type of light may be or comprise one or more of a continuous wave or pulsed wave. For example, light of a first spectral band of the pre-selected type of light may be a pulsed wave and light of a second spectral band of the pre-selected type of light may be a continuous wave.

In another example embodiment, the pre-selected type of light may include one or more near-infrared spectral bands, in alternative to, or in addition to, visible spectral bands. Light in the near-infrared spectral bands may be detected by an image capture device, such as a camera. The surgical illumination system may include one or more such image capture devices configured to detect and image near-infrared light.

In an example embodiment, light in at least one visible spectral band of the pre-selected type of light may be a continuous wave and light in at least one near-infrared spectral band of the pre-selected type of light may be a pulsed wave. In another example embodiment, one or more visible spectral bands may be pulsed, and the near-infrared light may be continuous.

In an example embodiment, the surgical illumination system may comprise a despeckling element to reduce laser speckle. The despeckling element may be an active diffuser, and able to be switched on or off by the user during operation the surgical illumination system.

In an example embodiment, the pre-selected type of light may consist of or include two or three spectral bands each having a peak intensity wavelength, with a separation between the peak intensity wavelengths of adjacent spectral bands of the two or three spectral bands is at least 50 nm or more.

In an example implementation, the pre-selected type of light may include a central spectral band that is centered at no more than 625 nm; that is centered at between 590 nm to 610 nml that is centered at between 490 and 510 nm, that is centered at between 530 and 550 nm; that has a first spectral band at 415 nm and a second spectral band at 540 nm; that has a spectral band centered at 415 nm; that has a first spectral band centered at 625 nm and a second spectral band centered at 600 nm with the power at the first spectral band being equal to or less than the power at the second spectral band. In another example embodiment, the preselected type of light may have a spectral band centered have a spectral band centered at one or more of 730, 740, 750, 760, 770, 780, 785, 805, 808, or 850 nm.

In an example embodiment, the pre-selected type of light may include two adjacent spectral bands, wherein light intensity in a valley region disposed between the two adjacent spectral bands is less than 50% of light intensity of both of the adjacent spectral bands.

In an example embodiment, the pre-selected type of light may be a white light with a color temperature above 5000K.

In another example embodiment, the pre-selected type of light may include two adjacent spectral bands. A light intensity in a valley region disposed between the two adjacent spectral bands may be less than 50% of light intensity of both of the adjacent spectral bands.

According to another example embodiment of the present invention, a surgical illumination device for illuminating a target surgical area may aid tissue differentiation. The surgical illumination device may include, one or more of the features described above. The surgical illumination device may also include a plurality of selectable optical filers to remove pre-selected spectral bands from light provided by the surgical illumination device. The surgical illumination device may also include at least one turret for holding the plurality of selectable optical filters. The at least one turret may be actuatable or rotatable through a plurality of configurations. Each configuration may correspond to a set of optical filters from the plurality of selectable optical filters and a resulting type of filtered multispectral light, like the preselected type of light described above.

According to an example embodiment of the present invention, a medical method for illuminating a target surgical area may be used to aid tissue differentiation. The medical method may include providing a medical illumination device. The medical method may further include illuminating a target surgical area of a patient with light from the medical illumination device. The medical method may yet further include selecting a setting of the medical illumination device corresponding to a pre-selected type of light. The pre-selected type of light may be multispectral light with substantially no visible light emission beyond 650 nm. The medical method may also include observing with a human eye the target surgical area as illuminated by the medical illumination device. In an example embodiment, the pre-selected type of light may have any of the characteristics described above.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11 illustrates a schematic diagram of an illumination system, according to an example embodiment.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

The present invention will be described in relation to illumination of a surgical site. However, one skilled in the art will appreciate that this is not intended to be limiting and that the light sources described herein may be used in any number of other applications for illuminating other target work areas.

Figure 1:
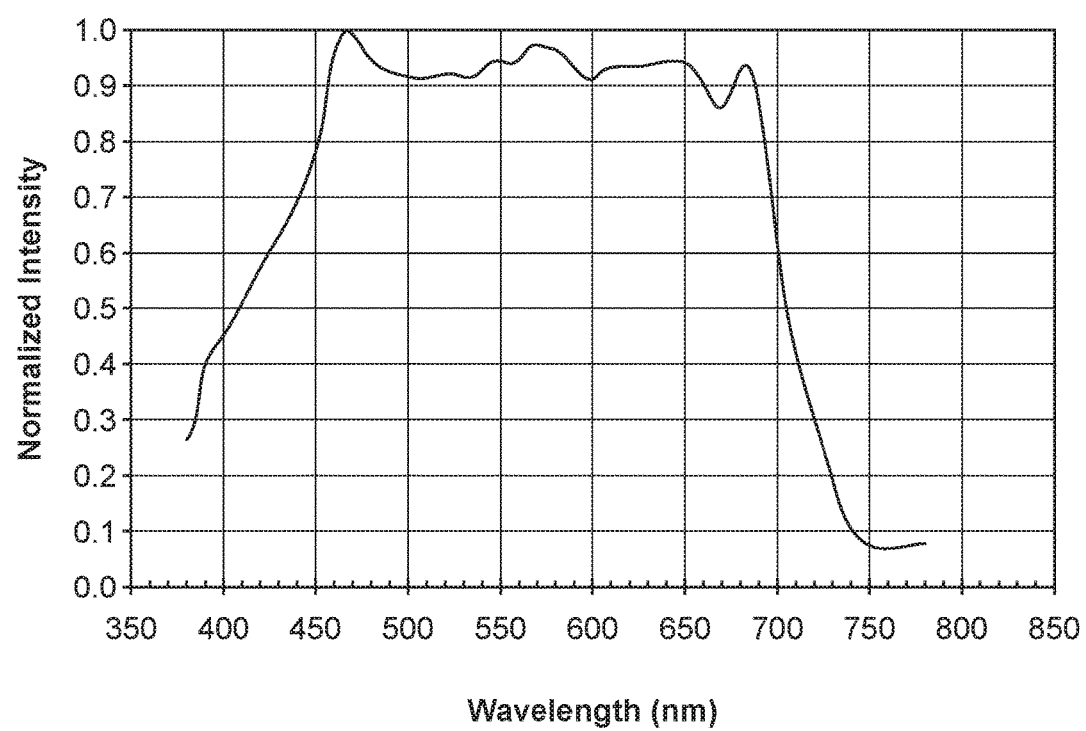
FIG. 1 shows a representative spectrum provided by a xenon light source, according to an example embodiment.
Figure 2:
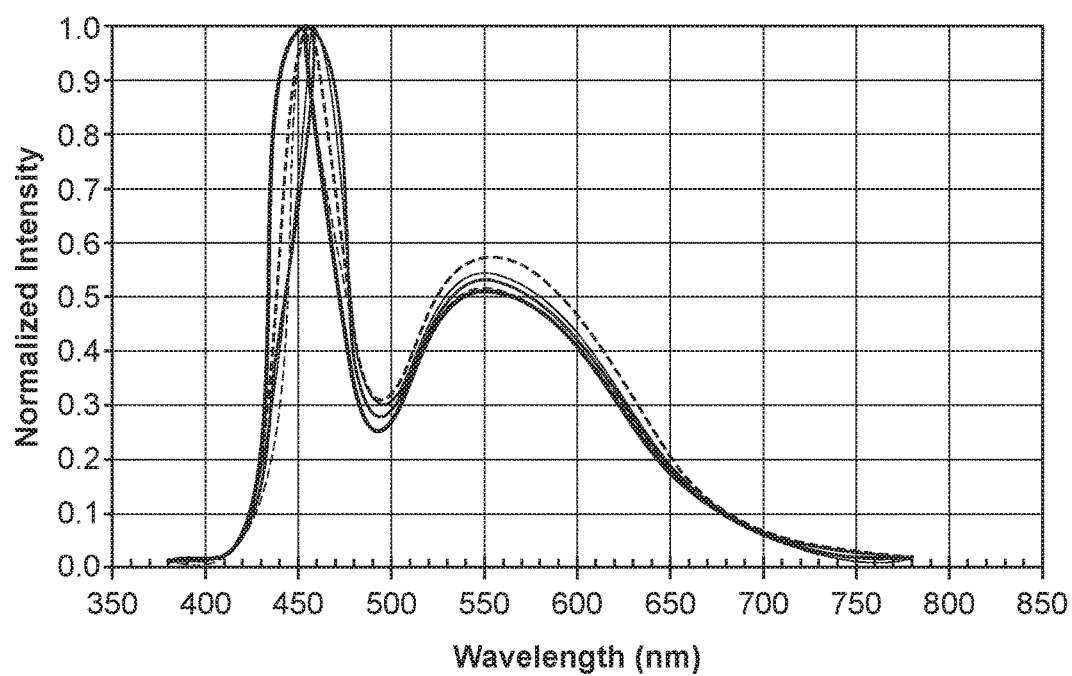
FIG. 2 shows a representative spectrum provided by a white light LED source, according to an example embodiment.
Figure 3:
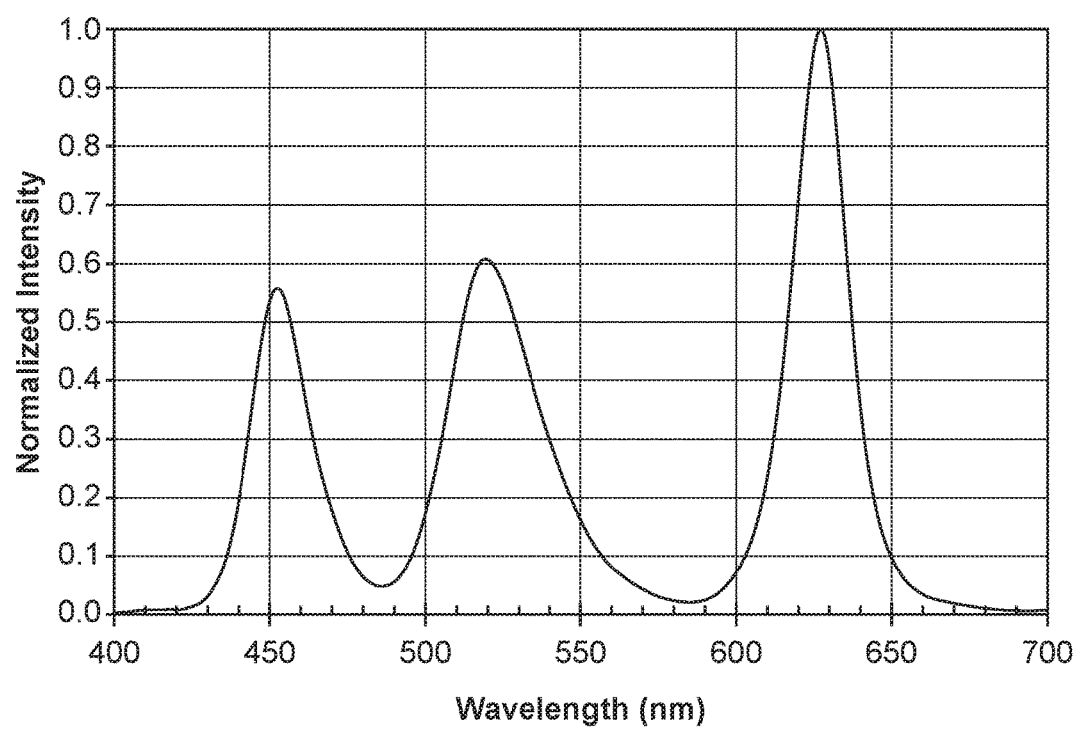
FIG. 3 illustrates a representative spectrum provided by a RGB LED light source, according to an example embodiment.

As discussed earlier, many commercially available light sources are either xenon- or LED-based. Some of the LED sources may provide standard white light having a broad white visible spectrum similar to xenon. The typical xenon spectrum looks similar to the graph in FIG. 1 where the y-axis is normalized intensity and the x-axis is wavelength. Also discussed previously, FIG. 2 illustrates the typical spectrum provided by a white light LED source where the y-axis is normalized intensity and the x-axis is wavelength, and FIG. 3 illustrates the typical spectrum provided by a RGB LED light source where the y-axis is normalized intensity and the x-axis is wavelength.

Figure 4:
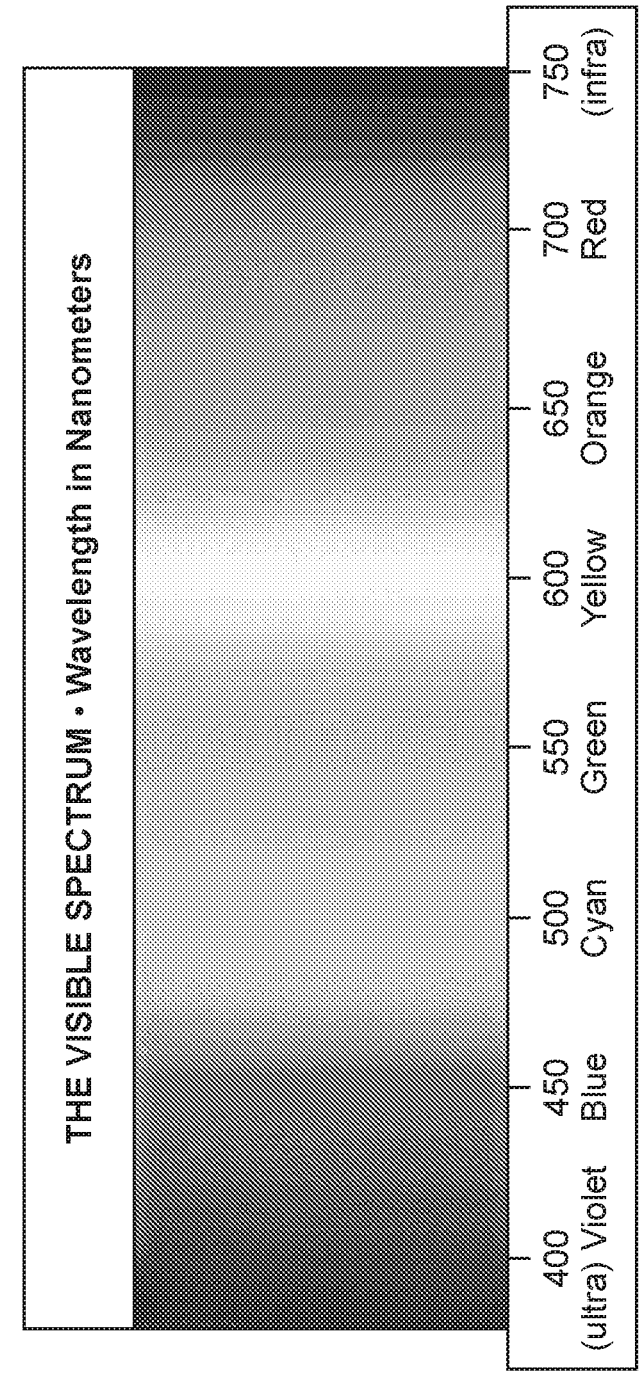
FIG. 4 illustrates the visible spectrum, according to an example embodiment.

In designing example embodiments of the light engine disclosed herein (also referred to herein as a light source or illumination source, and the like), spectral organization as well as reflection and absorption data were considered. FIG. 4 illustrates the color spectrum for visible light. It ranges from about 400 nm (violet) to about 700 nm (red). Nominal wavelengths and frequency intervals for various colors are summarized in Table 1 below.

TABLE 1

| Color | Wavelength Interval, nm | Frequency Interval, THz |
|---|---|---|
| Red | ~625-740 | ~480-405 |
| Orange | ~590-625 | ~510-480 |
| Yellow | ~565-590 | ~530-510 |
| Green | ~500-565 | ~600-530 |
| Cyan | ~485-500 | ~620-600 |
| Blue | ~440-485 | ~680-620 |
| Violet | ~80-440 | ~790-680 |

Figure 5:
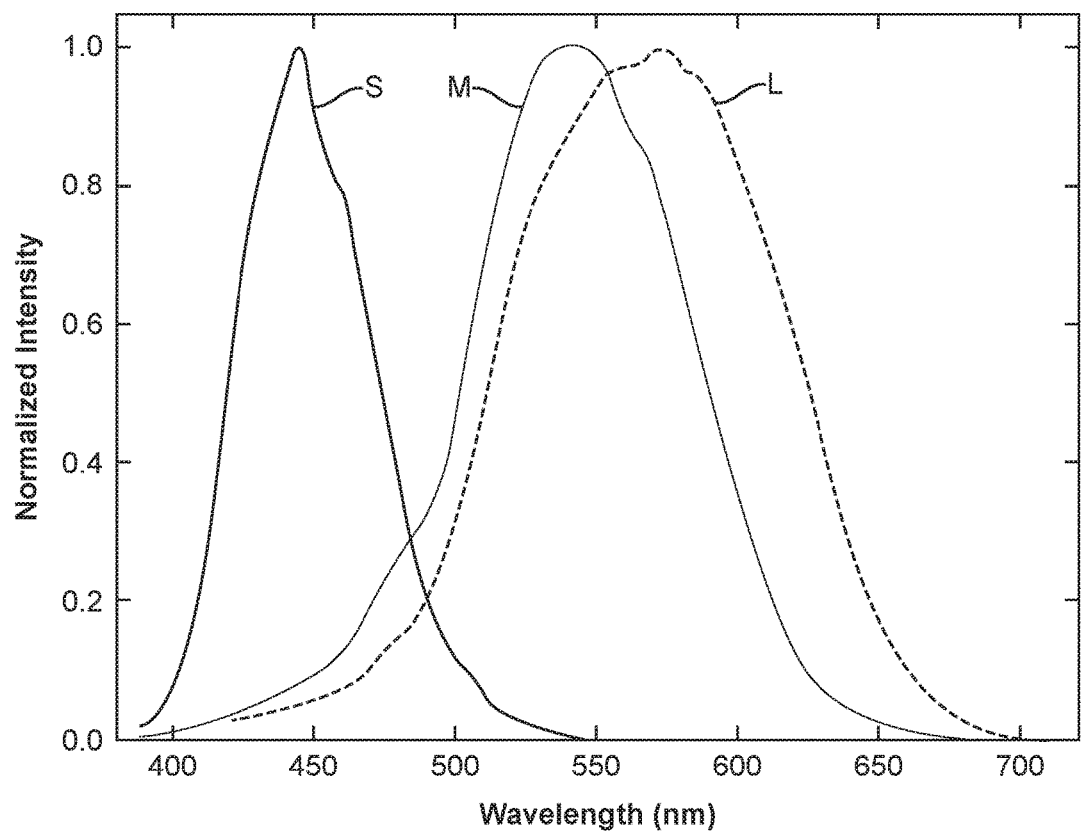
FIG. 5 illustrates the human eye response to various wavelengths of light, according to an example embodiment.

Human eye response and hemoglobin absorption and reflectance are also relevant. FIG. 5 shows the human eye response where it can be seen that past 650 nm, the eye response is low. On the spectrum, the majority of the red color is seen above 620 nm. The y-axis in FIG. 5 is normalized intensity and the x-axis is wavelength.

Figure 6:
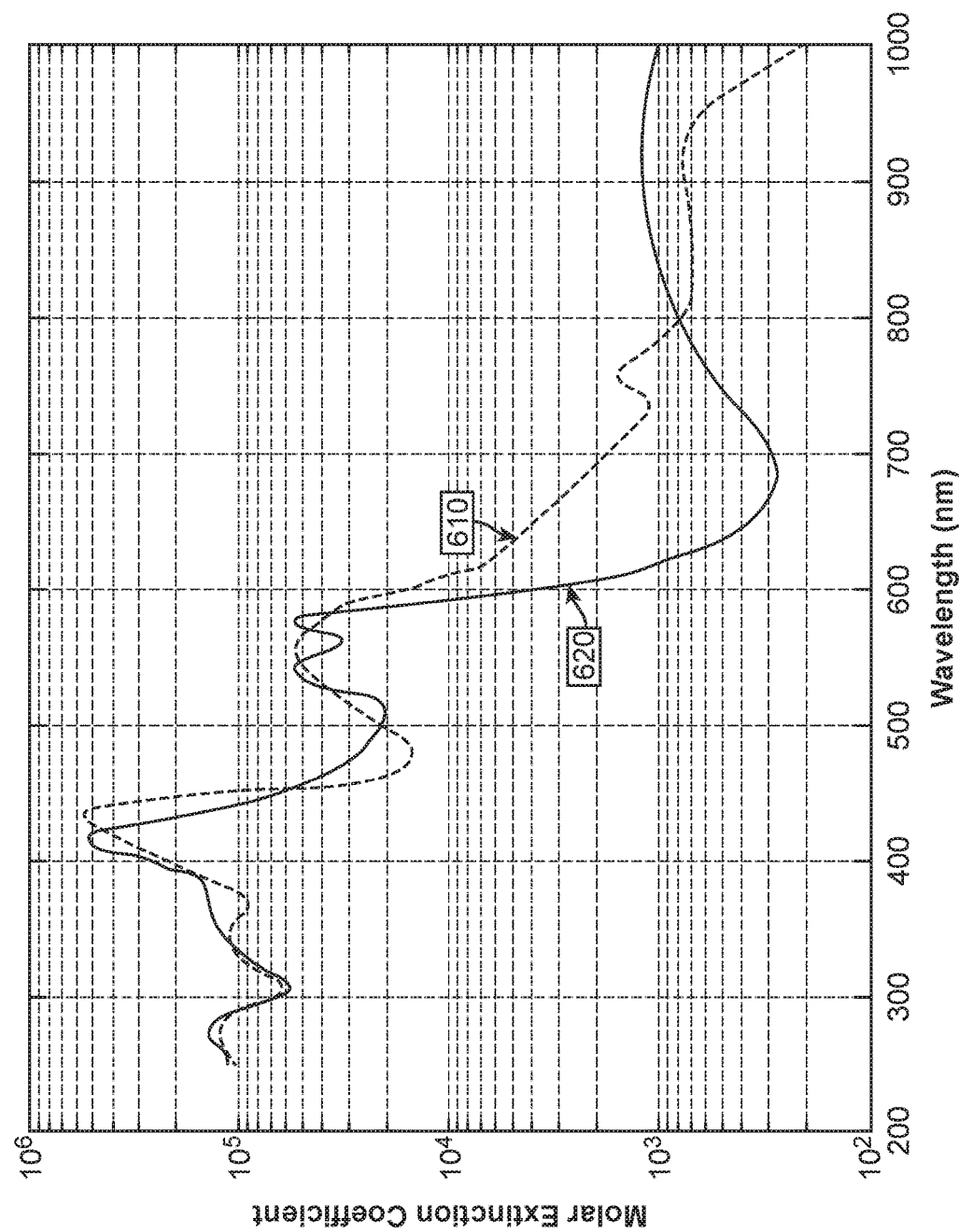
FIG. 6 illustrates the absorption spectra for hemoglobin in blood, according to an example embodiment.

FIG. 6 illustrates the absorption spectra for hemoglobin in blood. Oxygenated hemoglobin ($HbO_2$) is indicated by 620 and deoxygenated hemoglobin (Hb) is indicated by 610. Based on the absorption spectra, for a surgeon or other operator that wants to see vasculature, the vasculature in the region can be illuminated at approximately blue and green discrete bands (band centered at 415 nm for blue and band centered at 540 nm for green), according to an example embodiment. During surgery, much of the human tissue typically has a red color due to blood concentration. Therefore, a light engine is provided, according to an example embodiment, which reduces the reflectance of the blood, thereby providing better tissue contrast for a surgeon or operator.

Figure 7:
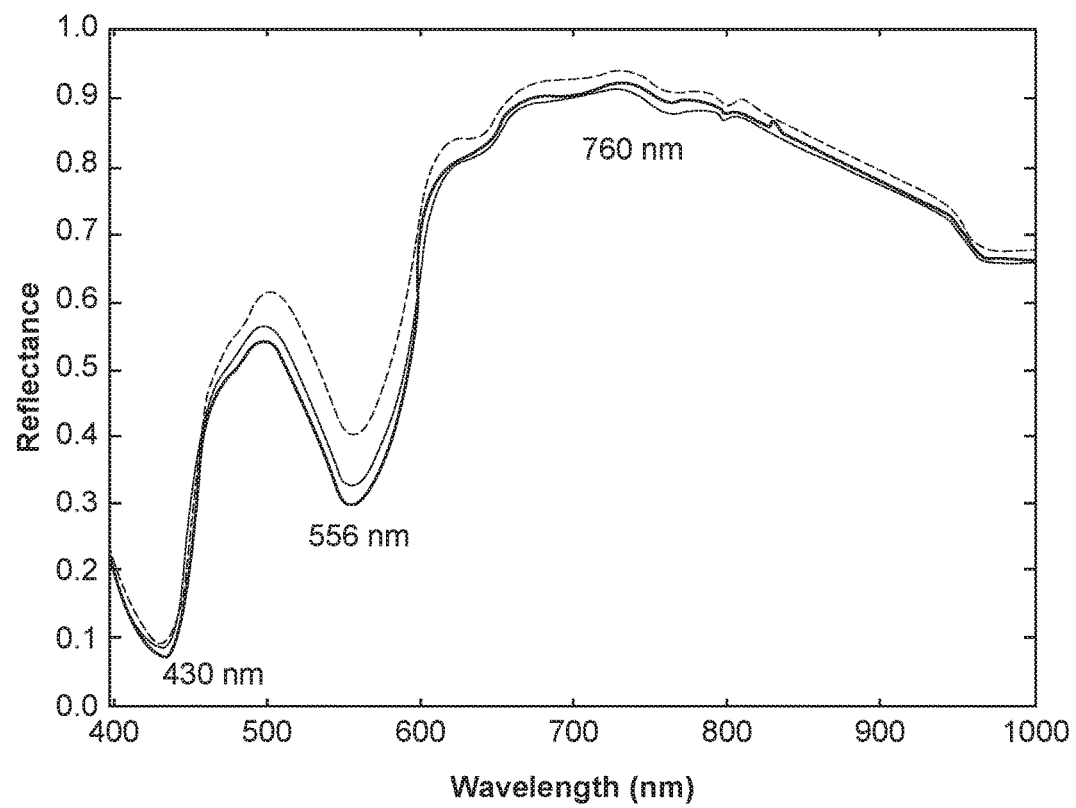
FIG. 7 illustrates reflectance of blood, according to an example embodiment.

FIG. 7 illustrates reflectance of blood which exhibits very strong attenuation of light below 625 nm and longer wavelengths. Hemoglobin has a strong reflectance band at 625 nm and longer wavelengths. These, and other, performance criteria were considered when developing example embodiments of a light engine that provides improved illumination of tissue, and thus visual differentiation, in the surgical field.

Figure 8A:
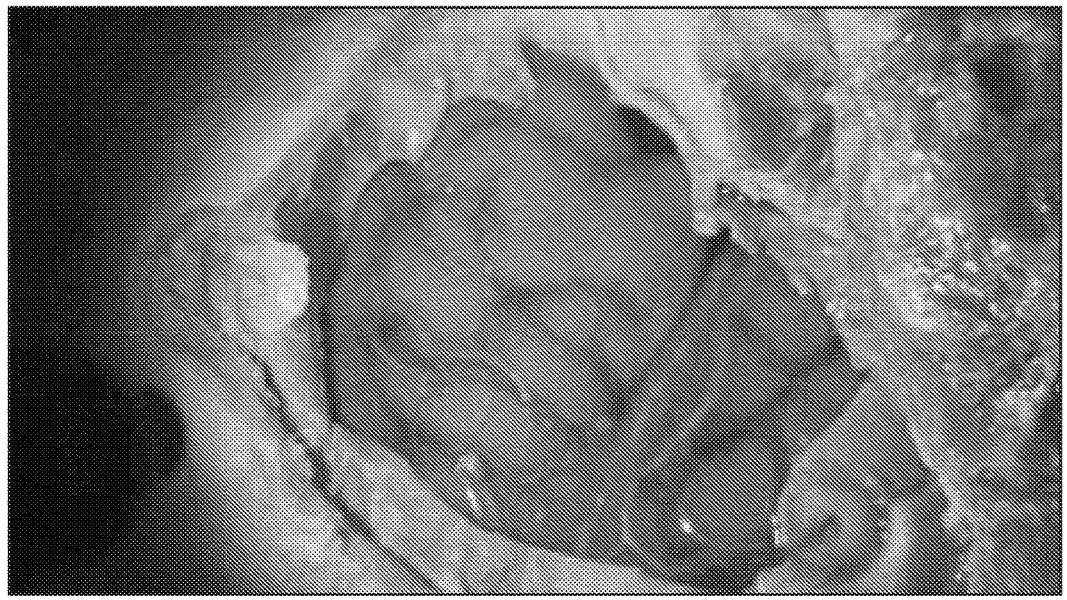
FIG. 8A illustrates a surgical image before any red spectrum is removed, according to an example embodiment.
Figure 8B:
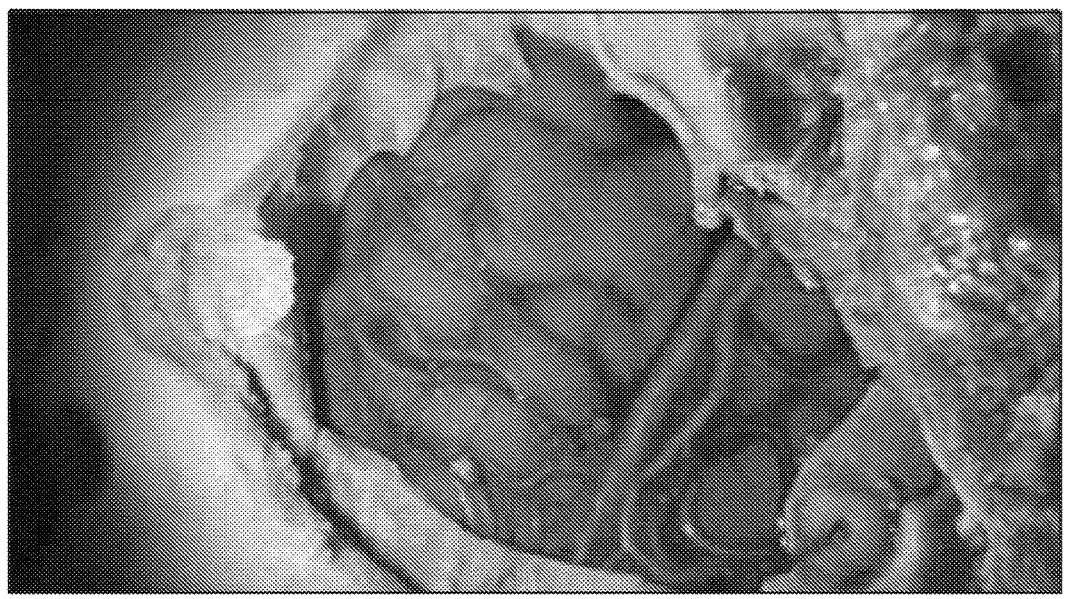
FIG. 8B illustrates the after effect when a portion of the red spectrum is removed from the surgical image of FIG. 8A, according to an example embodiment.

FIG. 8A illustrates an image of tissue illuminated with standard white light. FIG. 8B illustrates the same tissue area with a portion of the red spectrum removed, which provides better contrast and therefore a better view of the anatomy. As shown by FIGS. 8A and 8B, surgeons with direct visualization of a patient's tissue during open surgery may benefit in particular from various example embodiments of the present invention.

According to an example embodiment, a light engine is provided which provides standard white light. For example, there may be a setting which can easily be actuated to provide standard white light with a color temperature above 5000K and CRI above 85. This example embodiment may be combined with any other example embodiments disclosed herein.

Other features of the light engine may include a light output setting that is constructed by two or three discrete color LEDs, one or more filtered lamps, one or more lasers or other illumination sources, or a combination thereof. Additional illumination elements may be used to provide more discrete color. In another example embodiment, the light source may have a setting which is constructed by two or three spectral bands only, such as seen in FIG. 3. Some example embodiments may provide light with no light emission past 650 nm and the spectral band may be centered no further than 625 nm. In example embodiments with a band centered at 625 nm, the power level of the output may be equal to or lower than the power of a light source having band at 600 nm.

Other example embodiments have a band centered around 590 nm to 610 nm. Some example embodiments may have at least one spectral band centered around 490 nm to 510 nm. Other example embodiments may have a spectral band centered around 415 nm, or between 530 nm to 550 nm. Still other example embodiments may have a setting that provides central spectral bands at 415 nm and 540 nm. One skilled in the art will appreciate that any combination of these features may be made in the light source provided.

One example embodiment may provide light with non-visible light emission past 650 nm. For example, near-infrared light may be emitted beyond the visual spectrum, for example, between 730 and 900 nm. In some example embodiments, the light may have a spectral band centered at 730, 740, 750, 760, 770, 780, 785, 805, 808, or 850 nm. The near-infrared light may be detected and imaged by a camera or other image capture device.

In some example embodiments, the light provided by the light source may be a continuous or pulsed wave. Moreover, individual spectral bands of a multispectral light source may be a continuous wave, or pulsed at a respective frequency. Thus, in an example embodiment, for a single light source, one or more spectral bands in the visible light range may be continuous waves, and one or more spectral bands in the near-infrared range may be pulsed.

In some example embodiments, when the light source provides a light output having two or three spectral bands, there may be a minimum separation between the edge of a first such band and the nearest edge of an adjacent band. This separation may be at a minimum of 50 nm from the center of one band to the center of the adjacent band. Also in some example embodiments, the intensity between two primary spectral bands in a valley region is less than 50% of the intensity of both adjacent bands.

Experimental Results:

FIGS. 9A-9F illustrate measured spectra for light output based on various illumination settings having some or all of the features described herein. Each of these settings show performance of a particular setting on the light source which controls the light output. The spectrum of FIG. 9A for example, corresponds to three LEDs, each with a different intensity. The major bands show separation and no light is delivered past 650 nm. The intensity in the valley between the bands is lower than 50% of the intensity of the both of the adjacent bands.

Figure 9A:
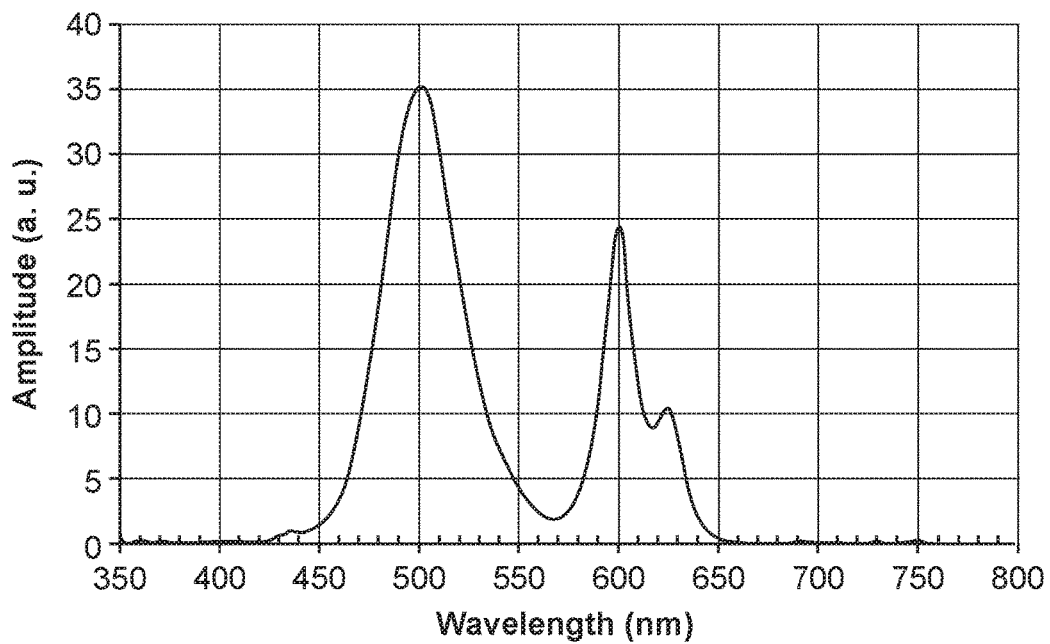
FIGS. 9A-9F illustrate spectra of light output from example embodiments of a light source.
Figure 9B:
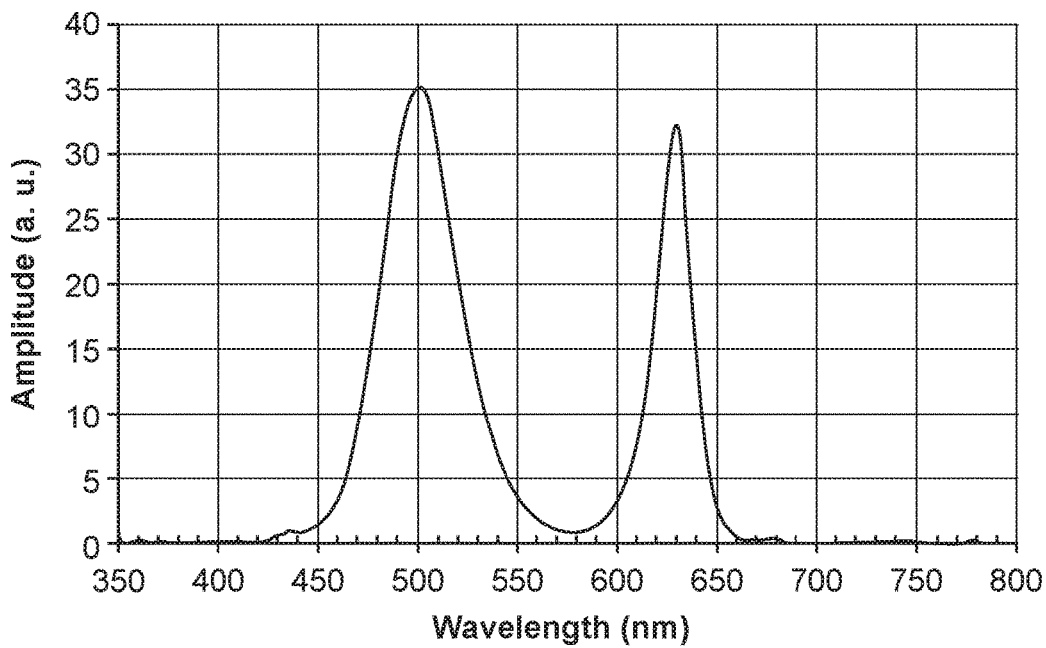
Figure 9C:
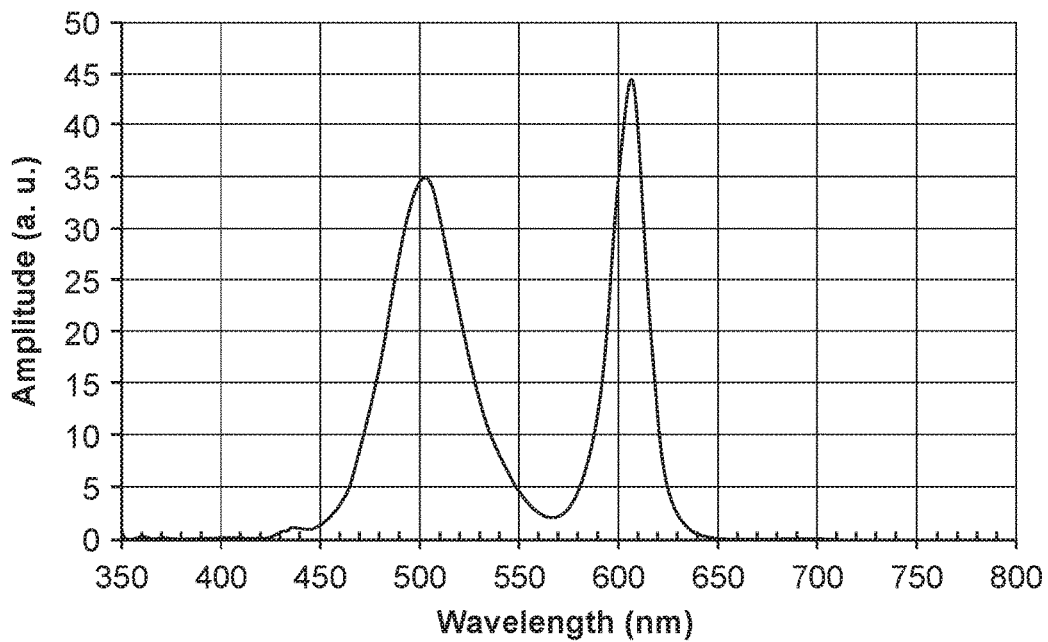
Figure 9D:
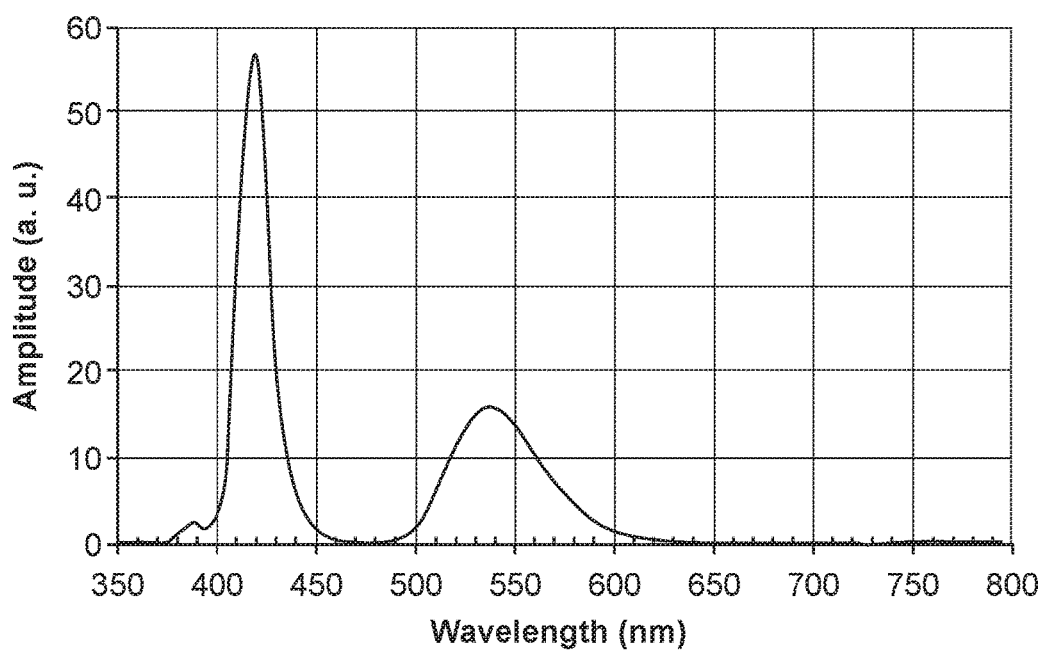
Figure 9E:
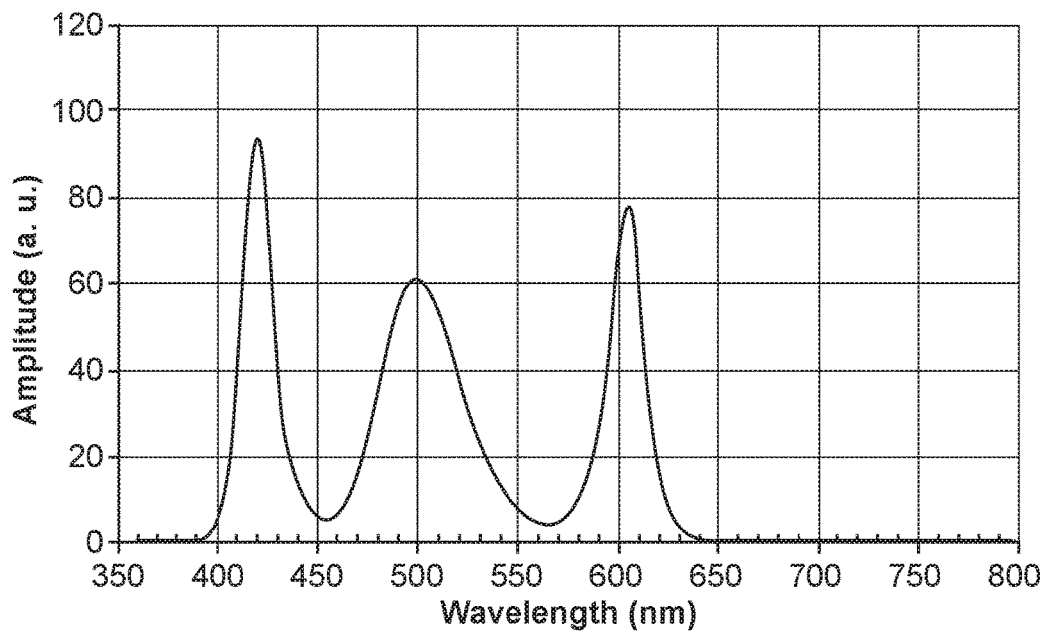
Figure 9F:
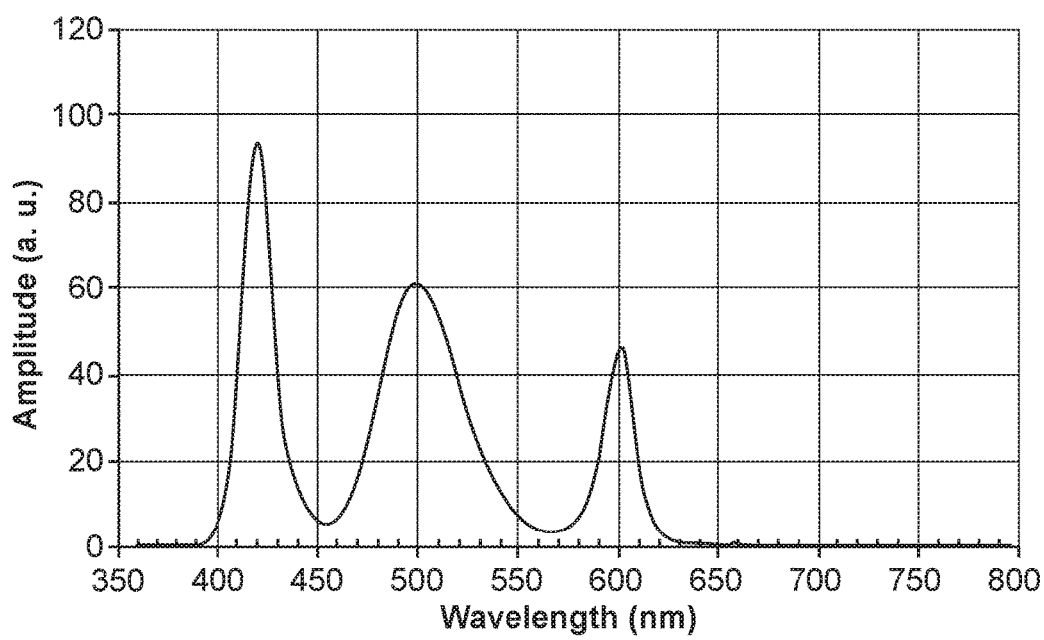

In FIG. 9B, the setting provides light that again only shows two bands produced by two discrete LEDs. The red content is reduced and a minimum separation of 50 nm is maintained between the bands. FIG. 9C corresponds to a similar setup, where again only two LEDs are used to produce two bands with minimum separation and no transmission past 650 nm. FIG. 9D corresponds to a setting that enhances blood/vasculature tissue. Since the local maximums of blood absorption are at 415 nm and 540 nm, the LED outputs may be centered at these bands and thus provide enhanced differentiation of blood or blood tissue. FIGS. 9E and 9F correspond to three illumination element setups, as previously described.

FIG. 11 illustrates a schematic diagram of an example embodiment of a surgical illumination system 1102. The system 1102 includes a light source 1104 which may have any of the features described in this specification. The light source includes one or more LED light sources 1106 such as white or red, green and blue LEDs to create white light, or lasers or filtered broadband light sources. Alternatively, or in addition, specific band LEDs may be included such as 415, 540, 500, 600, 625 nm. Preset buttons 1110 or other actuatable elements 1110 (also referred to as settings) may be disposed on the housing to the light source and may be actuated to provide preset lighting (e.g., spectra, intensity, etc.) such as those described above. There may be also be a wireless or wired controller to allow the surgeon to control settings. The controller may also be integrated into the cable, which can be disposable.

In another example embodiment, the actuatable elements 1110 may allow a user to manually adjust the light settings. A power cord 1108 optionally allows electrical coupling of the light source 1104 with a power outlet. The system may also include an optional light cable 1112 such as a fiber optic cable which transmits light from the light source to an optional illumination element 1114, which provides the desired light 1116 to the target work area. The illumination element may be any device which illuminates the work area such as a surgical instrument with an optical waveguide for illumination of a surgical work area.

Figure 10:
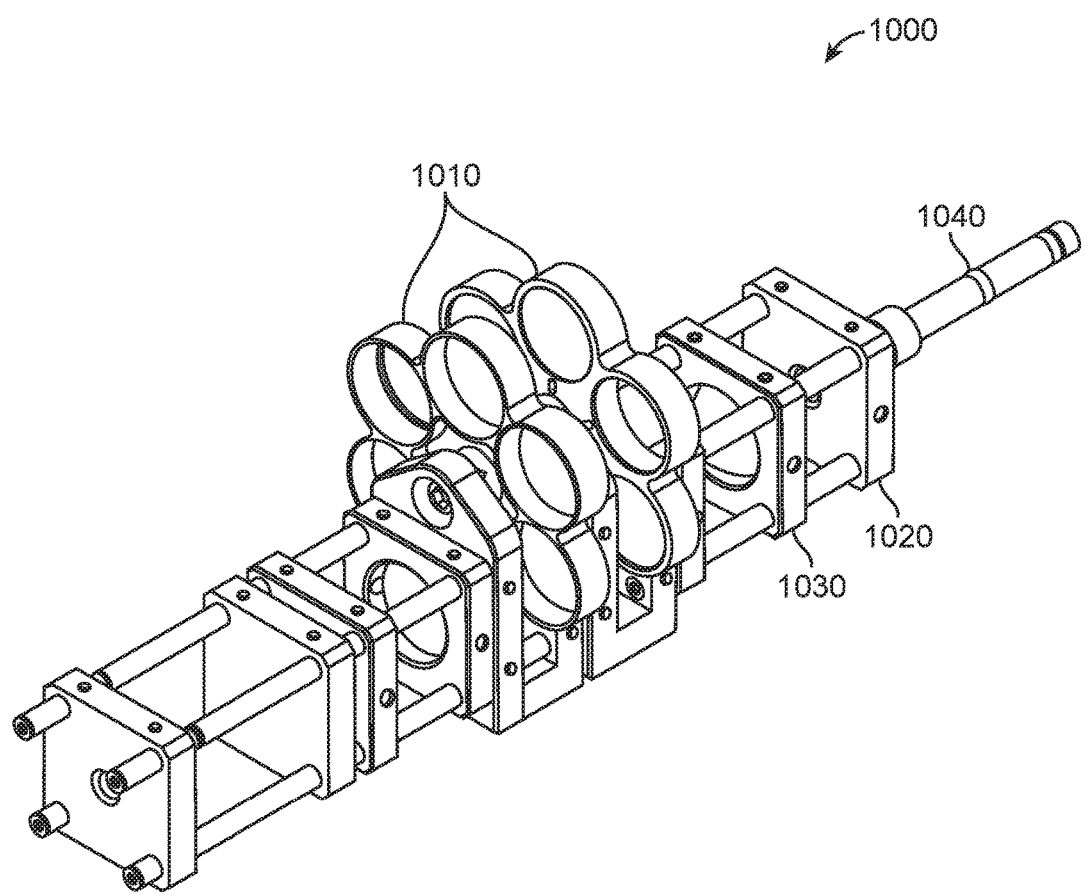
FIG. 10 illustrates a perspective view of an illumination system, according to an example embodiment.

FIG. 10 illustrates a perspective view of an illumination system, according to an example embodiment. As shown in FIG. 10, the illumination system may include a bridge through which light from an illumination source may be directed and collimated at a first stage of optics 1020. In some example embodiments, the illumination system may further include an angle-tuned pre-filter 1030.

The illumination system may include one or more optic filters for removing or reducing certain spectral bands from light. One skilled in the art will appreciate that an optic filter may not completely eliminate or block a particular spectral band. However, light in that spectral band may still be reduced by the filter to a nominal or insignificant intensity relative to the primary spectral bands of the light source. Accordingly, this disclosure may refer to substantially all of a spectral band being blocked or not being emitted by a light source.

In an example embodiment, a plurality of selectable optical filters may be held in one or more turrets 1010, or other structures, as shown in FIG. 10. Each turret may be rotatable into discrete positions, with each position corresponding to a particular combination of optic filters and thus a light setting. In some example embodiments, the turrets may be manually rotated. In other example embodiments, the turrets may be mechanically or electronically moved, for example by button or remote.

In some example embodiments, the illumination system may comprise a despeckling element for removing or reducing a laser speckle pattern. The despeckling element may be an active element, and may be turned on or off, according to an example embodiment. In another example embodiment, the despeckling element may be a passive diffuser.

While certain embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. For example, an illumination system may provide any range or ranges of light described herein and the light source may be any one or a combination of the light sources or elements described herein. It is intended that the following claims define the scope of the invention and that methods and structures within the scope of these claims and their equivalents be covered thereby.

What is claimed is:

1. A surgical illumination device for illuminating a target surgical area to aid tissue differentiation, said surgical illumination device comprising:
   at least one illumination source configured to generate light;
   a plurality of optical filters, wherein each optical filter is configured to substantially remove a pre-selected spectral band from the light when the light passes through the optical filter; and
   a plurality of turrets coupled to the plurality of optical filters,
   wherein each turret is rotatable, about an axis parallel to a transmission path of the light, among a plurality of positions,
   wherein the plurality of positions of the plurality of turrets define a plurality of spectral configuration settings,
   wherein each spectral configuration setting corresponds to a respective subset of the plurality of optical filters being aligned with the transmission path of the light such that the light passes through the respective subset of the plurality of optical filters and is transformed into a respective type of filtered multispectral light,
   wherein, for at least one of the plurality of spectral configuration settings, the respective subset of the plurality of optical filters causes the filtered multispectral light to comprise substantially no visible light emission beyond 650 nm,
   wherein the plurality of turrets comprises:
      a first turret rotatable, about the axis parallel to the transmission path of the light, among a plurality of first positions; and a second turret rotatable, about an axis parallel to the transmission path of the light, among a plurality of second positions wherein the plurality of optical filters comprises a plurality of first optical filters and a plurality of second optical filters, wherein the plurality of first optical filters are coupled to the first turret with each first optical filter at a respective location around the axis, wherein the plurality of second optical filters are coupled to the second turret with each second optical filter at a respective location around the axis, and wherein each subset of the plurality of optical filters comprises one of the plurality of first optical filters and one of the plurality of second optical filters.

2. The surgical illumination device of claim 1, wherein the at least one illumination source comprises two or more distinct illumination elements.

3. The surgical illumination device of claim 1, wherein the at least one illumination source comprises two discrete color light-emitting diodes (LEDs).

4. The surgical illumination device of claim 1, wherein, for at least one of the plurality of spectral configuration settings, the respective subset of the plurality of optical filters causes the filtered multispectral light to have a preselected type of light consisting of two or three spectral bands.

5. The surgical illumination device of claim 4, wherein the two or three spectral bands each have a peak intensity wavelength, and wherein a separation between peak intensity wavelengths of adjacent spectral bands of the two or three spectral bands is at least 50 nm.

6. The surgical illumination device of claim 1, wherein, for at least one of the plurality of spectral configuration settings, the respective subset of the plurality of optical filters causes the filtered multispectral light to have a preselected type of light having a central spectral band that is centered at no more than 625 nm.

7. The surgical illumination device of claim 1, wherein, for at least one of the plurality of spectral configuration settings, the respective subset of the plurality of optical filters causes the filtered multispectral light to have a preselected type of light comprising two adjacent spectral bands, and wherein a light intensity in a valley region between the two adjacent spectral bands is less than 50% of a light intensity of both of the two adjacent spectral bands.

8. The surgical illumination device of claim 1, wherein, for at least one of the plurality of spectral configuration settings, the respective subset of the plurality of optical filters causes the filtered multispectral light to have a preselected type of light that is white light with a color temperature above 5000K.

9. The surgical illumination device of claim 1, wherein, for at least one of the plurality of spectral configuration settings, the respective subset of the plurality of optical filters causes the filtered multispectral light to have a preselected type of light having a spectral band centered at between 590 nm to 610 nm.

10. The surgical illumination device of claim 1, wherein, for at least one of the plurality of spectral configuration settings, the respective subset of the plurality of optical filters causes the filtered multispectral light to have a preselected type of light having a spectral band centered between 490 nm and 510 nm.

11. The surgical illumination device of claim 1, wherein, for at least one of the plurality of spectral configuration settings, the respective subset of the plurality of optical filters causes the filtered multispectral light to have a preselected type of light having a spectral band centered between 530 nm and 550 nm.

12. The surgical illumination device of claim 1, wherein, for at least one of the plurality of spectral configuration settings, the respective subset of the plurality of optical filters causes the filtered multispectral light to have a preselected type of light having a first spectral band centered at 415 nm and a second spectral band centered at 540 nm.

13. The surgical illumination device of claim 1, wherein, for at least one of the plurality of spectral configuration settings, the respective subset of the plurality of optical filters causes the filtered multispectral light to have a preselected type of light having a spectral band centered at 415 nm.

14. The surgical illumination device of claim 1, wherein, for at least one of the plurality of spectral configuration settings, the respective subset of the plurality of optical filters causes the filtered multispectral light to have a preselected type of light comprising a first spectral band and a second spectral band, and wherein the first spectral band is centered at 625 nm, and the second spectral band is centered at 600 nm, and wherein power at the first spectral band is equal to or less than power at the second spectral band.

15. The surgical illumination device of claim 1, wherein, for at least one of the plurality of spectral configuration settings, the respective subset of the plurality of optical filters causes the filtered multispectral light to comprise substantially no light emission between 650 nm and 730 nm.

16. The surgical illumination device of claim 1, wherein, for at least one of the plurality of spectral configuration settings, the respective subset of the plurality of optical filters causes the filtered multispectral light to be configured to reduce reflection from blood relative to full-spectrum light.

17. The surgical illumination device of claim 1, wherein, for at least one of the plurality of spectral configuration settings, the respective subset of the plurality of optical filters causes the filtered multispectral light to be configured to aid tissue differentiation as viewed by a human eye in an open-surgery settings.

18. The surgical illumination device of claim 1, wherein, for at least one of the plurality of spectral configuration settings, the respective subset of the plurality of optical filters causes the filtered multispectral light to comprise a near-infrared spectral band for imaging by an image capture device.

19. The surgical illumination device of claim 18, further comprising the image capture device configured to detect near-infrared light.

20. The surgical illumination device of claim 18, wherein, for at least one of the plurality of spectral configuration settings, the respective subset of the plurality of optical filters causes the filtered multispectral light to have at least one visible spectral band of a continuous wave and at least one near-infrared spectral band of a pulsed wave.

21. The surgical illumination device of claim 1, wherein the at least one illumination source comprises at least one of a discrete color light-emitting diode (LED), a laser, or a filtered broadband light source.

22. The surgical illumination device of claim 1, wherein, for at least one of the plurality of spectral configuration settings, the respective subset of the plurality of optical filters causes the filtered multispectral light to comprise at least one spectral band that is a continuous wave.

23. The surgical illumination device of claim 1, wherein, for at least one of the plurality of spectral configuration settings, the respective subset of the plurality of optical filters causes the filtered multispectral light to comprise at least one spectral band that is a pulsed wave.

24. The surgical illumination device of claim 1, further comprising a despeckling element to reduce laser speckle.

25. The surgical illumination device of claim 1, further comprising a collimator configured to collimate the light between the illumination source and the plurality of optical filters.

26. The surgical illumination device of claim 25, further comprising an angle-tuned pre-filter between the collimator and the plurality of optical filters.

27. A medical method for illuminating a target surgical area to aid tissue differentiation, said medical method comprising:
   providing a medical illumination device comprising:
      at least one illumination source configured to generate light,
      a plurality of optical filters, wherein each optical filter is configured to substantially remove a pre-selected spectral band from the light when the light passes through the optical filter, and
      a plurality of turrets coupled to the plurality of optical filters,
      wherein each turret is rotatable, about an axis parallel to a transmission path of the light, among a plurality of positions,
      wherein the plurality of positions of the plurality of turrets define a plurality of spectral configuration settings,
      wherein each spectral configuration setting corresponds to a respective subset of plurality of optical filters being aligned with the transmission path of the light such that the light passes through the respective subset of the plurality of optical filters and is transformed into a respective type of filtered multispectral light,
      wherein the plurality of turrets comprises:
         (i) a first turret rotatable, about the axis parallel to the transmission path of the light, among a plurality of first positions; and
         (ii) a second turret rotatable, about an axis parallel to the transmission path of the light, among a plurality of second positions
      wherein the plurality of optical filters comprises a plurality of first optical filters and a plurality of second optical filters,
      wherein the plurality of first optical filters are coupled to the first turret with each first optical filter at a respective location around the axis,
      wherein the plurality of second optical filters are coupled to the second turret with each second optical filter at a respective location around the axis, and
      wherein each subset of the plurality of optical filters comprises one of the plurality of first optical filters and one of the plurality of second optical filters;
   selecting a spectral configuration setting from among the plurality of spectral configuration settings, wherein selecting the spectral configuration setting comprises rotating the plurality of turrets about the axis to position the respective subset of the plurality of optical filters, which corresponds to the spectral configuration setting, in alignment with the transmission path of the light; and
   after selecting the spectral configuration setting, illuminating a target surgical area of a patient with the respective type of filtered multispectral light for the spectral configuration setting from the medical illumination device,
   wherein, for at least one of the plurality of spectral configuration settings, the respective subset of the plurality of optical filters causes the filtered multispectral light to comprise substantially no visible light emission beyond 650 nm.

28. The medical method of claim 27, wherein the respective type of filtered multispectral light for the spectral configuration setting comprises substantially no light emission between 650 nm and 730 nm.

29. The medical method of claim 27, wherein the respective type of filtered multispectral light for the spectral configuration setting is configured to reduce reflection from blood relative to full-spectrum light.

30. The medical method of claim 27, wherein the respective type of filtered multispectral light for the spectral configuration setting is configured to aid tissue differentiation as viewed by a human eye in an open-surgery setting.

31. The medical method of claim 27, wherein the respective type of filtered multispectral light for the spectral configuration setting comprises a near-infrared spectral band for imaging by an image capture device.

32. The medical method of claim 27, wherein the at least one illumination source of the medical illumination device comprises at least one a discrete color light-emitting diode (LED), a laser, or a filtered broadband light source.

33. The medical method of claim 27, wherein the respective type of filtered multispectral light for the spectral configuration setting comprises a pre-selected type of light comprising at least one spectral band that is a continuous wave.

34. The medical method of claim 27, wherein the respective type of filtered multispectral light for the spectral configuration setting comprises a pre-selected type of light comprising at least one spectral band that is a pulsed wave.

* * * * *